(12) United States Patent  
Yoshihara et al.

(10) Patent No.: US 12,409,145 B2  
(45) Date of Patent: Sep. 9, 2025

(54) GRANULE, PREPARATION CONTAINING THE GRANULE, PRODUCTION METHOD OF THE GRANULE, AND PRODUCTION METHOD OF PREPARATION CONTAINING THE GRANULE

(71) Applicant: SAWAI PHARMACEUTICAL Co., Ltd., Osaka (JP)

(72) Inventors: Naoki Yoshihara, Osaka (JP); Ryota Kimata, Osaka (JP)

(73) Assignee: SAWAI PHARMACEUTICAL CO., LTD., Osaka (JP)

( * ) Notice: Subject to any disclaimer, the term of this patent is extended or adjusted under 35 U.S.C. 154(b) by 60 days.

(21) Appl. No.: 17/470,096

(22) Filed: Sep. 9, 2021

(65) Prior Publication Data

US 2022/0071913 A1 Mar. 10, 2022

Related U.S. Application Data

(60) Provisional application No. 63/076,654, filed on Sep. 10, 2020.

(30) Foreign Application Priority Data

Sep. 8, 2021 (JP) ................................. 2021-146436

(51) Int. Cl.
*A61K 9/50* (2006.01)
*A61K 9/16* (2006.01)
(Continued)

(52) U.S. Cl.
CPC ............ *A61K 9/5073* (2013.01); *A61K 47/10* (2013.01); *A61K 47/32* (2013.01)

(58) Field of Classification Search
None
See application file for complete search history.

(56) References Cited

U.S. PATENT DOCUMENTS 9,095,513 B2 * 8/2015 Tanji ................... A61K 9/5042  
2019/0054029 A1 2/2019 Hayashida et al.

FOREIGN PATENT DOCUMENTS

EP 3324948 B1 * 2/2023 ............. A61K 31/18  
JP 2006-176461 A 7/2006  
(Continued)

OTHER PUBLICATIONS

Office Action dated Apr. 8, 2025 for corresponding Japanese Patent Application No. 2021-146436, along with an English translation (8 pages).

*Primary Examiner* — Lakshmi S Channavajjala  
(74) *Attorney, Agent, or Firm* — Hauptman Ham, LLP (57) ABSTRACT

One of the objects of the present invention is to provide a granule capable of sufficiently masking bitterness. Alternatively, one of the objects of the present invention is to provide a preparation containing a granule capable of sufficiently masking bitterness. According to an embodiment of the present invention, a granule is provided including a core substance on which a melt component and an active ingredient are disposed, a gelling substance-containing layer disposed on a surface where the melt component and the active ingredient are disposed, and a hydrophobic polymer-containing layer disposed on a surface of the gelling substance-containing layer.

6 Claims, 3 Drawing Sheets

(51) Int. Cl.
  *A61K 47/10* (2017.01)
  *A61K 47/32* (2006.01)

(56) References Cited

FOREIGN PATENT DOCUMENTS

| JP | 2007-524646 A | 8/2007 | |
|---|---|---|---|
| JP | 2012-87073 A | 5/2012 | |
| WO | 02/096392 A1 | 12/2002 | |
| WO | 2005/009410 A2 | 2/2005 | |
| WO | WO-2006102964 A2 * | 10/2006 | ............... A61K 9/20 |
| WO | 2011/121823 A1 | 10/2011 | |
| WO | WO-2015063670 A1 * | 5/2015 | ............. A61K 31/55 |
| WO | WO-2017146052 A1 * | 8/2017 | ........... A61K 31/135 |

* cited by examiner

GRANULE, PREPARATION CONTAINING THE GRANULE, PRODUCTION METHOD OF THE GRANULE, AND PRODUCTION METHOD OF PREPARATION CONTAINING THE GRANULE

CROSS-REFERENCE TO RELATED APPLICATIONS

This application is based upon and claims the benefit of priority from the Provisional Application No. 63/076,654, filed on Sep. 10, 2020, and the prior Japanese Patent Application No. 2021-146436, filed on Sep. 8, 2021, the entire contents of which are incorporated herein by reference.

FIELD

An embodiment of the present invention relates to a granule for masking the bitterness of an active ingredient or a preparation containing the granule. Alternatively, an embodiment of the present invention relates to a production method of a granule for masking the bitterness of an active ingredient or a production method of the preparation containing the granule.

BACKGROUND

Although many active ingredients which exhibit bitterness are known, the release of the active ingredient in an oral cavity can cause severe discomfort to a patient and significantly reduce medication compliance. The release of the active ingredient from a drug should be inhibited, at least while the drug is present in the oral cavity.

Conventionally, masking of bitterness has been performed by covering an active ingredient-containing layer with a taste masking layer containing a water-insoluble polymer, for example, as described in WO02/096392.

WO2017/146052 describes a pharmaceutical composition particle including a core particle containing a drug, an intermediate layer containing a water-soluble gelling swelling substance to coat an outside of the core particle, and an outer layer containing a water-insoluble substance to coat an outside of the intermediate layer, for the purpose of achieving both shielding of an unpleasant taste and improvement of an elution property.

In WO02/096392 and WO2017/146052, although bitterness is masked by coating the active ingredient-containing composition, in the case of an active ingredient having strong bitterness, it is necessary to thicken a coating layer. In this case, there is a problem whereby the pharmaceutical composition particle after coating becomes large and the feeling of actual taking drug is lost. In addition, in a case where the coating layer is thickened, the coating time becomes longer by that amount, and manufacturing efficiency is degraded. Therefore, there is a need for a preparation which can be easily prepared and which is easy to take while being capable of masking bitterness.

SUMMARY

One of the objects in an embodiment of the present invention is to provide a granule capable of sufficiently masking bitterness. Alternatively, one of the objects in an embodiment of the present invention is to provide a preparation containing the granule capable of sufficiently masking bitterness. Alternatively, one of the objects in an embodiment of the present invention is to provide a production method of the granule capable of sufficiently masking bitterness. Alternatively, one of the objects in an embodiment of the present invention is to provide a production method of the preparation containing the granule capable of sufficiently masking bitterness.

According to an embodiment of the present invention, there is provided a granule including a core substance disposed with a melt component and an active ingredient, a gelling substance-containing layer disposed on a surface where the melt component and the active ingredient are disposed, and a hydrophobic polymer-containing layer disposed on a surface of the gelling substance-containing layer.

The granule may further include a melt component layer containing the melt component and disposed on a surface of the core substance, and an active ingredient-containing layer including the melt component and the active ingredient may be disposed on the surface of the melt component layer.

The granule may further include an overcoat layer disposed on a surface of the hydrophobic polymer-containing layer.

The gelling substance-containing layer may include a gelling substance having a viscosity of 10 mPa/s or more in a 2% aqueous solution.

The gelling substance-containing layer may include one or more gelling substances selected from a group consisting of sodium carboxymethyl cellulose, polyethylene oxide, sodium polyacrylate, sodium alginate, propylene glycol alginate, xanthan gum, carrageenan, guar gum, tara gum, pectin, hydroxypropyl cellulose, hydroxyethyl cellulose, methyl cellulose, carboxyvinyl polymer, locust bean gum, tamarind seed gum, gum arabic, karaya gum, agar, gelatin, polyvinyl alcohol, and a copolymer with polyvinyl alcohol as a part.

The hydrophobic polymer-containing layer may include one or more hydrophobic polymers selected from ethyl cellulose, acetyl cellulose, cellulose acetate phthalate, carboxymethyl ethyl cellulose, hydroxypropyl methyl cellulose acetate succinate, hydroxypropyl methyl cellulose phthalate, dimethylaminoethyl methacrylate/methyl methacrylate copolymer, methyl acrylate/methacrylate acid copolymer, ethyl acrylate/methyl methacrylate copolymer dispersion, aminoalkyl methacrylate copolymer RS, dried methacrylic acid copolymer LD, aminoalkyl methacrylate copolymer E, methacrylic acid copolymer L, methacrylic acid copolymer S, and polyvinyl acetal diethylaminoacetate.

The content ratio of the gelling substance contained in the gelling substance-containing layer to the hydrophobic polymer contained in the hydrophobic polymer-containing layer may be in a range of 2:3 to 3:8.

According to an embodiment of the present invention, there is provided a preparation including any of the above granules and one or more pharmaceutically acceptable additives.

According to an embodiment of the present invention, there is provided a production method of a granule including disposing a melt component and an active ingredient on a surface of a core substance, forming a gelling substance-containing layer by disposing a gelling substance by dry coating on a surface where the melt component and the active ingredient are disposed, and forming a hydrophobic polymer-containing layer by disposing a hydrophobic polymer on a surface of the gelling substance-containing layer.

A melt component layer may be further formed containing the melt component and disposed on a surface of the core substance, and an active ingredient-containing layer may be formed containing the melt component and the active ingredient on a surface of the melt component layer.

An overcoat layer may be further formed on a surface of the hydrophobic polymer-containing layer.

The gelling substance-containing layer may include a gelling substance having a viscosity of 10 mPa/s or more in a 2% aqueous solution.

The gelling substance-containing layer may include one or more gelling substances selected from a group consisting of sodium carboxymethyl cellulose, polyethylene oxide, sodium polyacrylate, sodium alginate, propylene glycol alginate, xanthan gum, carrageenan, guar gum, tara gum, pectin, hydroxypropyl cellulose, hydroxyethyl cellulose, methyl cellulose, carboxyvinyl polymer, locust bean gum, tamarind seed gum, gum arabic, karaya gum, agar, gelatin, polyvinyl alcohol, and a copolymer with polyvinyl alcohol as a part.

The hydrophobic polymer-containing layer may include one or more hydrophobic polymers selected from ethyl cellulose, acetyl cellulose, cellulose acetate phthalate, carboxymethyl ethyl cellulose, hydroxypropyl methyl cellulose acetate succinate, hydroxypropyl methylcellulose phthalate, dimethylaminoethyl methacrylate/methyl methacrylate copolymer, methyl acrylate/methacrylic acid copolymer, ethyl acrylate/methyl methacrylate copolymer dispersion, aminoalkyl methacrylate copolymer RS, dried methacrylic acid copolymer LD, aminoalkyl methacrylate copolymer E, methacrylic acid copolymer L, methacrylic acid copolymer S, and polyvinyl acetal diethylaminoacetate.

The content ratio of the gelling substance contained in the gelling substance-containing layer to the hydrophobic polymer contained in the hydrophobic polymer-containing layer may be in a range of 2:3 to 3:8.

According to an embodiment of the present invention, there is provided a production method of the preparation including mixing a granule produced by the production method described in any of the above and one or more pharmaceutically acceptable additives.

DESCRIPTION OF EMBODIMENTS

Hereinafter, a granule according to the present invention and a preparation using the same will be described with reference to the drawings. The granule of the present invention and the preparation using the same are not to be construed as being limited to the description of the embodiments and examples shown below. In the drawings referred to in the present embodiment and the examples to be described later, the same portions or portions having similar functions are denoted by the same symbols, and a repetitive description thereof is omitted.

Figure 1:
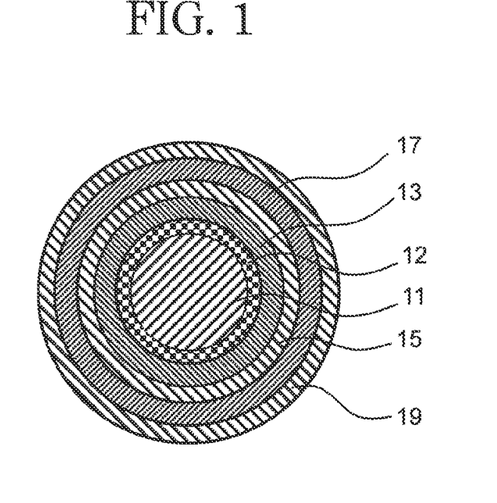
FIG. 1 is a schematic view showing a cross-sectional structure of a granule 10 according to an embodiment of the present invention.

FIG. 1 is a schematic view (cross-sectional view) showing a granule 10 according to an embodiment of the present invention. The granule 10 includes a core substance 11, a melt component layer 12 disposed on a surface of the core substance 11, an active ingredient-containing layer 13 disposed on a surface of the melt component layer 12, a gelling substance-containing layer 15 disposed on a surface of the active ingredient-containing layer 13, a hydrophobic polymer-containing layer 17 disposed on a surface of the gelling substance-containing layer 15, and an overcoat layer 19 disposed on a surface of the hydrophobic polymer-containing layer 17. In the case where the adhesive property between the core substance 11 and the active ingredient-containing layer 13 is good, the melt component layer 12 may be omitted. The overcoat layer 19 may also be omitted.

The core substance 11 is a carrier for disposing the melt component layer 12, the active ingredient-containing layer 13, the gelling substance-containing layer 15, the hydrophobic polymer-containing layer 17, and the overcoat layer 19. The core substance 11 is a substance which serves as a core for disposing the melt component layer 12, the active ingredient-containing layer 13, the gelling substance-containing layer 15, the hydrophobic polymer-containing layer 17, and the overcoat layer 19 in producing the granule 10. In order to obtain an adhesive property with the melt component layer 12, an adsorbent material is used as the core substance 11. For example, an adsorbent material composed of amberlite IRP-64, ion exchange resin, kaolin, calcium carmellose, hydrous silicon dioxide, magnesium silicate, light anhydrous silicic acid, light liquid paraffin, diatomaceous earth, synthetic aluminum silicate, aluminum oxide, aluminum hydroxide, absorbent cotton, magnesium carbonate, precipitated calcium carbonate, dextrin, silicon dioxide, composite aluminum silicate potassium grain, bentonite, polyethylene fiber, magnesium aluminate metasilicate, and medicinal charcoal, and the like can be used as the core substance 11.

The core substance 11 is preferably spherical so as to uniformly dispose the melt component layer 12, the active ingredient-containing layer 13, the gelling substance-containing layer 15, the hydrophobic polymer-containing layer 17. and the overcoat layer 19.

The melt component layer 12 is a layer disposed between the core substance 11 and the active ingredient-containing layer 13. The melt component layer 12 is a base layer for disposing the active ingredient-containing layer 13. In the case where the active ingredient itself has strong adhesive property to the core substance or the ability of the core substance to carry the active ingredient is high, then the melt component and the active ingredient may be disposed directly on the core substance. On the other hand, by arranging the melt component layer 12 composed of a melt component having a high adhesive property to the core substance 11 on the surface of the core substance 11, more active ingredients can be adhered to the melt component layer 12, and the content of the active ingredient in the granule 10 can be effectively increased.

The melt component (first melt component) constituting the melt component layer 12 can be selected from oil-based additives. The first melt component is preferably selected from additives in which contacts with the active ingredient do not denature the active ingredient or exhibit a significant increase in related substances. The melt component layer 12 is preferably formed by a melt layering method, and the first melt component may be selected from additives which are solid at normal temperature. Considering the temperature range generally used in the melt layering method, the first melt component is preferably selected from additives having a melting point of 100° C. or less and is preferably selected from additives having a melting point in a temperature range in which the active ingredient does not denature or exhibit a significant increase in related substances. Additives having such properties are exemplified by glycerin monostearate, macrogol (polyethylene glycol), lauromacrogol, and stearic acid, but not limited thereto.

The melt component layer 12 may be disposed on the surface of the core substance 11 in an amount capable of disposing the active ingredient-containing layer 13 and may be disposed on at least a part of the surface of the core substance 11. It is preferable that the melt component layer 12 covers 90% or more of the surface of the core substance 11 and preferably covers the entire surface of the core substance 11. Although there is no particular limitation on the thickness of the melt component layer 12, it is preferable that the thickness of the melt component layer 12 is as thin as possible from the viewpoint of increasing the active ingredient content per granule 10. In an embodiment, it is preferable that the first melt component constituting the melt component layer 12 is also disposed in a pore of the core substance 11. In an embodiment, the interface between the core substance 11 and the melt component layer 12 may have a structure in which the melt component constituting the melt component layer 12 enters from the surface of the core substance 11. In this case, the core substance 11 and the melt component layer 12 do not need to have a clear interface. By arranging the melt component not only on the surface of the core substance 11 but also in the pore connecting to the surface of the core substance 11, an anchoring effect on the core substance 11 is imparted to the melt component layer 12, and the adhesive property of the melt component layer 12 to the core substance 11 is improved.

The active ingredient-containing layer 13 is a layer containing the active ingredient and the melt component and may be disposed on the surface of the core substance 11 or may be disposed via the melt component layer 12. In the granule 10, the active ingredient is not particularly limited.

In the case where the melt component layer 12 is disposed on the surface of the core substance 11, a second melt component is included in the active ingredient-containing layer 13 to bind the active ingredients to each other and to bind the active ingredient to the surface of the melt component layer 12. The second melt component is preferably selected from additives in which contacts with the active ingredient do not denature the active ingredient or exhibit a significant increase in related substances. Since the active ingredient-containing layer 13 is formed by the melt layering method, the second melt component is selected from additives which are solid at normal temperature. When the temperature range generally used in the melt layering method is considered, the second melt component is preferably selected from additives having a melting point of 100° C. or less, or a glass transition point of 120° C. or less and is preferably selected from additives having a melting point or a glass transition point in a temperature range in which the active ingredient is not denatured or exhibits a significant increase in related substances. In the case where an additive having a melting point or glass transition point lower than the melting point of the first melting component is selected as the second melting component, when the active ingredient-containing layer 13 is formed by the melt layering method, the active ingredient-containing layer 13 can be disposed on the surface of the melt component layer 12 without significantly affecting the surface structure of the melt component layer 12 or changing the surface structure of the melt component layer 12. On the other hand, in the case where an additive having a melting point or glass transition point higher than the melting point of the first melt component is selected as the second melt component, when the active ingredient-containing layer 13 is formed by the melt layering method, the surface of the melt component layer 12 is slightly melted, and the interface between the melt component layer 12 and the active ingredient-containing layer 13 is fused, so that the adhesive property of the active ingredient-containing layer 13 to the melt component layer 12 can be improved.

The additive used as the second melting component can be exemplified by stearic acid, glyceryl monostearate, macrogol (polyethylene glycol), carnauba wax, hydrogenated oil, lauromacrogol, palmitic acid, cetyl alcohol, aminoalkyl methacrylate copolymer E, ammonioalkyl methacrylate copolymer, dried methacrylic acid copolymer, hypromellose acetate succinate ester, polyvinylpyrrolidone, and polyvinyl acetal diethyl aminoacetate, and the like, but not limited thereto. The melt component (second melt component) contained in the active ingredient-containing layer 13 may be the same as or different from the melt component (first melt component) contained in the melt component layer 12.

The active ingredient-containing layer 13 contains the active ingredient as the main component. The active ingredient-containing layer 13 preferably contains 50% by mass or more of the active ingredient relative to the sum of the masses of the active ingredient and the second melt component. In other words, it is preferable that for the active ingredient-containing layer 13 contain a small amount of the second melt component within a range in which the active ingredient-containing layer 13 can be formed on the surface of the melt component layer 12. Thus, the content of the active ingredient in the granule 10 can be effectively increased.

The gelling substance-containing layer 15 has a function for adjusting the elution of the active ingredient from the active ingredient-containing layer 13. As will be described later, although the hydrophobic polymer-containing layer 17 suppresses moisture (saliva) in the oral cavity from flowing into the active ingredient-containing layer 13, the gelling substance contained in the gelling substance-containing layer 15 absorbs moisture soaked from the hydrophobic polymer-containing layer 17 and gelates to form a gel layer. This gel layer can suppress the influx of moisture into the active ingredient containing layer 13 in the oral cavity to prevent elution of the active ingredient from the active ingredient containing layer 13. In addition, since a large amount of water in the gastric juice dissolves the gel layer, the gelling substance-containing layer 15 can achieve rapid elution of the active ingredient from the active ingredient-containing layer 13 in the stomach.

In this embodiment, a gelling substance having a viscosity of 10 mPa/s or more in a 2% aqueous solution can be used. For example, one gelling substance or a combination of two or more gelling substances selected from sodium carboxy methylcellulose, polyethylene oxide, sodium polyacrylate, sodium alginate, propylene glycol alginate, xanthan gum, carrageenan, guar gum, tara gum, pectin, hydroxypropyl cellulose, hydroxyethyl cellulose, methyl cellulose, carboxyvinyl polymer, locust bean gum, tamarind seed gum, arabic gum, karaya gum, agar, gelatin, polyvinyl alcohol, and a copolymer with polyvinyl alcohol as a part and the like may be used as the gelling substance.

The hydrophobic polymer-containing layer 17 has a function for suppressing moisture in the oral cavity from flowing into the active ingredient-containing layer 13. The hydrophobic polymer-containing layer 17 is composed of a water-insoluble substance which is hardly soluble in water or practically insoluble in water. For example, one hydrophobic polymer or a combination of two or more hydrophobic polymers selected from ethyl cellulose, acetyl cellulose, cellulose acetate phthalate, carboxymethyl cellulose, hydroxypropyl methyl cellulose acetate succinate, hydroxypropyl methylcellulose phthalate, dimethylaminoethyl methacrylate/methyl methacrylate copolymer, methyl acrylate/methacrylic acid copolymer, ethyl acrylate/methyl methacrylate copolymer dispersion, aminoalkyl methacrylate copolymer RS, dried methacrylic acid copolymer LD, aminoalkyl methacrylate copolymer E, methacrylic acid copolymer L, methacrylic acid copolymer LD, methacrylic acid copolymer S, and polyvinyl acetal diethylaminoacetate and the like may be used as the water-insoluble substance.

In the granule 10 according to the embodiment, it is possible to sufficiently suppress moisture in the oral cavity from flowing into the active ingredient-containing layer 13 by having the gelling substance-containing layer 15. Therefore, the hydrophobic polymer-containing layer 17 can be thinned. The time required for producing the granule 10 can be reduced by thinning the hydrophobic polymer-containing layer 17. In addition, for the granule 10 according to the embodiment, since the gelling substance-containing layer 15 is disposed by the melt layering method, it is possible to greatly reduce the time required for the arrangement of the gelling substance-containing layer 15 as compared with the conventional case.

By arranging the overcoat layer 19 on the surface of the hydrophobic polymer-containing layer 17, the ingestibility is improved and the elution delay of the active ingredient is suppressed. For example, one or a combination of two or more selected from pregelatinized starch, sodium caseinate, carboxyvinyl polymer, carboxymethyl starch sodium, sucrose fatty acid ester, hydroxypropyl cellulose, hydroxypropyl methyl cellulose, methyl cellulose, hydroxyethyl cellulose, pullulan, polyvinylpyrrolidone, copolyvidone, polyoxyethylene-polyoxypropylene glycol, polyvinyl alcohol-polyethylene glycol graft copolymer, polyvinyl alcohol, macrogol, polyethylene oxide, amino acids such as glycine and alanine, sweeteners such as glycyrrhizic acid, sugars such as dextrin and lactose, sugar alcohols such as mannitol and xylitol, crystalline cellulose, crospovidone, and triethyl citrate and the like may be used for the overcoat layer 19.

[Production Method of Granule]

The granule 10 according to an embodiment of the present invention can be produced as follows. The core substance 11 and the first melt component are mixed, and the first melt component is disposed on the surface of the core substance 11. In addition, the first melt component is melted by the melt layering method to form the melt component layer 12 on the surface of the core substance 11. At this time, the core substance 11 and the first melt component are heated to a temperature equal to or higher than the melting point of the first melt component. Considering the temperature range generally used in the melt layering method, the heating temperature is 100° C. or less. Further, by arranging the first melt component not only on the surface of the core substance 11 but also in the pore connecting to the surface of the core substance 11, it is preferable to impart an anchoring effect on the core substance 11 to the melt component layer 12 and improve the adhesive property of the melt component layer 12 to the core substance 11.

The core substance 11 disposed with the melt component layer 12 is mixed with the active ingredient and the second melt component, and the active ingredient and the second melt component are disposed on the surface of the melt component layer 12. Further, the second melt component is melted by the melt layering method to form the active ingredient-containing layer 13 on the surface of the melt component layer 12. At this time, the core substance 11 disposed with the melt component layer 12, the active ingredient, and the second melt component are heated to a temperature equal to or higher than the melting point of the second melt component. Considering the temperature range generally used in the melt layering method, the heating temperature is 100° C. or less.

In an embodiment, in the case where an additive having a melting point or glass transition point lower than the melting point of the first melting component is selected as the second melting component, when the active ingredient-containing layer 13 is formed by the melt layering method, the active ingredient-containing layer 13 can be formed on the surface of the melt component layer 12 without significantly affecting the surface structure of the melt component layer 12 or changing the surface structure of the melt component layer 12 by heating to a temperature equal to or higher than the melting point or glass transition point of the second melting component and lower than the melting point of the first melting component. On the other hand, in the case where an additive having a melting point or glass transition point higher than the melting point of the first melt component is selected as the second melt component, when the active ingredient-containing layer 13 is formed by the melt layering method, the surface of the melt component layer 12 is slightly melted by heating to a temperature higher than the melting point or glass transition point of the second melt component, and the interface between the melt component layer 12 and the active ingredient-containing layer 13 is fused, so that the adhesive property of the active ingredient-containing layer 13 to the melt component layer 12 can be improved. It is preferable to fuse layers in a temperature range that does not denature the active ingredient or exhibit a significant increase in related substances.

A gelling substance is disposed on the surface of the active ingredient-containing layer 13. In this embodiment, the gelling substance-containing layer 15 is formed by dry coating. In an embodiment, the gelling substance-containing layer 15 can be suitably formed by the melt layering method.

The hydrophobic polymer-containing layer 17 is disposed on the surface of the gelling substance-containing layer 15. The hydrophobic polymer-containing layer 17 can be formed by coating a hydrophobic polymer on the surface of the gelling substance-containing layer 15 using a mixed solvent of a hydrophilic organic solvent and water. For example, ethanol, isopropanol, or the like can be suitably used as the hydrophilic organic solvent. It is preferable to use a mixed solvent in the range of water:organic solvent=1:2 to 1:100.

The overcoat layer 19 is disposed on the surface of the hydrophobic polymer-containing layer 17. The overcoat layer 19 can be formed by coating the above-described additive on the surface of the hydrophobic polymer-containing layer 17 using an aqueous solvent such as water or a non-aqueous solvent such as alcohol.

In this embodiment, since the gelling substance-containing layer 15 is formed between the active ingredient-containing layer 13 and the hydrophobic polymer-containing layer 17, the hydrophobic polymer-containing layer 17 can be thinned. The time required for producing the granule 10 can be reduced by thinning the hydrophobic polymer-containing layer 17. In the granule 10 according to the embodiment, since the gelling substance-containing layer 15 is disposed by the melt layering method, it is possible to greatly reduce the time required for the arrangement of the gelling substance-containing layer 15 as compared with the conventional case.

[Preparation]

A preparation using the granule 10 can be produced. For example, the granule 10 and one or more pharmaceutically acceptable known additives may be mixed to form a pharmaceutical composition. The pharmaceutical composition may be tableted to form a tablet. The pharmaceutical composition to which a disintegrant is added may be tableted to form an orally disintegrating tablet. The pharmaceutical composition may be encapsulated in a capsule to form a capsule tablet.

[Evaluation of Effect of Suppressing Bitterness]

The effect of suppressing bitterness of the granule 10 according to the present embodiment can be evaluated by a sensory test. The effect of suppressing bitterness of the preparation according to the present embodiment can be evaluated according to a dissolution test method (paddle method) of the Japanese Pharmacopoeia Seventeenth Edition.

Example 1

256 g of hydrous silicon dioxide (Fuji Silysia Chemical Ltd., Sylopure® P100) was used as the core substance 11, and 384 g of stearic acid (NOF CORPORATION, Sakura Fine Powder) was used as the first melt component. Hydrous silicon dioxide and stearic acid were poured into a high-speed stirring granulator (Fukae Industrial Co., Ltd., high-speed mixer, FS-GS-5 J), and granulated for 11 minutes at an agitator rotation speed of 300 rpm, a chopper rotation speed of 1500 rpm, and a water temperature of about 80° C. At this time, the temperature of the additive was about 70° C.

80.0 g of the core substance disposed with the melt component layer 12 on the surface, 248.12 g of sitagliptin phosphate as the active ingredient, and 24.0 g of aminoalkyl methacrylate copolymer E (Evonik Roehm, EUDRAGIT® EPO) as the second melt component were poured into a rotor fluidized bed granulator (Powrex Corporation, Model: MP-01) and granulated at an air supply temperature of 80.0 to 85.0° C. and a rotor rotation speed of 400 rpm. At this time, the temperature of the additive was about 60° C.

352.12 g of the core substance disposed with the active ingredient-containing layer 13 on the surface, 32.0 g of carboxy vinyl polymer (Lubrizol Advanced Materials, Inc., CARBOPOL® 971P NF), and 6.0 g of sucralose (San-Ei Gen F.F.I., Inc., P) were poured into a rotor fluidized bed granulator (Powrex Corporation, Model: MP-01), and dry coating was performed at an air supply temperature of 80.0 to 85.0° C. and a rotor rotation speed of 400 rpm. At this time, the temperature of the additive was about 60° C. CARBOPOL® 971P NF has a viscosity of 4000 to 11000 mPa/s in a 0.5% aqueous solution.

48.0 g of dried methacrylic acid copolymer LD (Evonik Roehm, EUDRAGIT® L100-55), 1.44 g of hypromellose (Shin-Etsu Chemical Co., Ltd., TC-5® E), 14.4 g of talc (FUJI TALC INDUSTRIAL CO., LTD., ML115), and 4.8 g of light anhydrous silicic acid (Freund Corporation, Adsolider® 101) were dispersed in 560 g of ethanol and 96.0 g of purified water to prepare a coating liquid. 390.12 g of the core substance disposed with the gelling substance-containing layer 15 on the surface was poured into a rotor fluidized bed granulator (Powrex Corporation, Model: MP-01) and sprayed with a coating agent to form the hydrophobic polymer-containing layer 17.

32.0 g of D-mannitol (Mitsubishi Shoji Foodtech Co., Ltd., Mannitol P) and 4.0 g of sucralose (San-Ei Gen F.F.I., Inc., P) were dissolved in 280 g of purified water to prepare a coating liquid. 458.76 g of the core substance disposed with the hydrophobic polymer-containing layer 17 on the surface was poured into a rotor fluidized bed granulator (Powrex Corporation, Model: MP-01) and sprayed with a coating agent to form the overcoat layer 19 to obtain the particle of Example 1.

140 mg of granules constituting of 113.4 mg of D-Mannitol (Mitsubishi Shoji Foodtech Co., Ltd, Mannitol P), 14.0 mg of crystalline cellulose (Asahi Kasei Corp., CEOLUS® PH-101), 7.0 mg of low substitution hydroxypropyl cellulose (Shin-Etsu Chemical Co., Ltd., L-HPC® NDB-022), 2.8 mg of crospovidone (BASF, Kollidon® CL-F), and 2.8 mg of crospovidone (BASF, Kollidon® CL-M), 247.38 mg of particles of Example 1, 34.62 mg of D-Mannitol (Freund Corporation, Granutol® F), 20.0 mg of silica-treated crystalline cellulose (JRS PHARMA, PROSOLV® SMCC50), 16.0 mg of crospovidone (BASF, Kollidon® CL-F), 10.0 mg of magnesium aluminometasilicate (Fuji Chemical Industries Co., Ltd., Neusilin® UFL-2), and 12.0 mg of sodium stearyl fumarate (Rettenmaier Japan, Co., Ltd., PRUVR) were mixed per tablet in a poly bag, and the mixed powder was tableted at a tableting pressure of 11.3 kN using a rotary tableting press (KIKUSUI SEISAKUSHO LTD., VELA5).

Comparative Example 1

Figure 2:
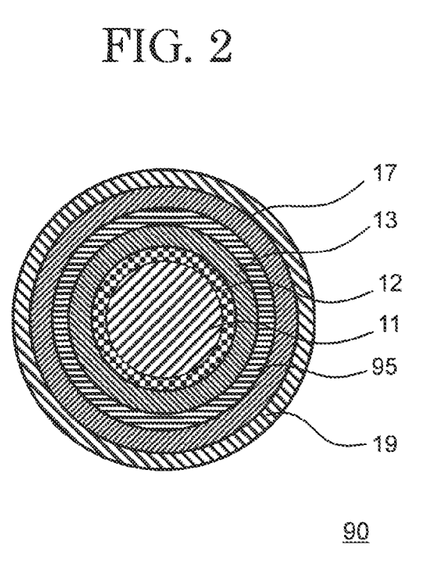
FIG. 2 is a schematic view showing a cross-sectional structure of a granule 90 of a comparative example.

FIG. 2 is a schematic view showing a cross section of a granule 90 of Comparative Example 1. The granule 90 of Comparative Example 1 is different from the granule 10 of Example 1 in that an undercoat layer 95 is disposed on the surface of the active ingredient-containing layer 13 instead of the gelling substance-containing layer 15.

32.0 g of hypromellose (Shin-Etsu Chemical Co., Ltd., TC-5® E) and 1.6 g of light anhydrous silicic acid (Freund Corporation, Adsolider® 101) were dispersed in 640 g of purified water to prepare a coating liquid. 352.12 g of the core substance disposed with the active ingredient-containing layer 13 on the surface obtained by the same method as in Example 1 was poured into a rotor fluidized bed granulator (Powrex Corporation, Model: MP-01) and sprayed with a coating agent to form the undercoat layer 95.

80.0 g of dried methacrylic acid copolymer LD (Evonik Roehm, EUDRAGIT® L100-55), 3.2 g of hypromellose (Shin-Etsu Chemical Co., Ltd., TC-5® E), 24.0 g of talc (FUJI TALK INDUSTRIAL CO., LTD., ML115), and 8.0 g of light anhydrous silicic acid (Freund Corporation, Adsolider® 101) were dispersed in 1000 g of ethanol and 200.0 g of purified water to prepare a coating liquid. 390.12 g of the core substance disposed with the undercoat layer 95 on the surface was poured into a rotor fluidized bed granulator (Powrex Corporation, Model: MP-01) and sprayed with a coating agent to form the hydrophobic polymer-containing layer 17.

The overcoat layer 19 was formed by the same method as in Example 1 to obtain the particle of Comparative Example 1.

138.68 mg of granules constituting of 103.68 mg of D-mannitol (mannitol P), 12.8 mg of crystalline cellulose (PH-101), 6.4 mg of low-substitution hydroxypropyl cellulose (NDB-022), 2.56 mg of crospovidone (CL-F), and 2.56 mg of crospovidone (CL-M), 278.46 mg of particles of Comparative Example 1, 35.54 mg of D-mannitol (Granutol® F), 16.0 mg of silica-treated crystalline cellulose (SMCC50), 10.0 mg of crospovidone (CL-F), 16.0 mg of magnesium aluminometasilicate (UFL-2), and 16.0 mg of sodium stearyl fumarate (PRUV) were mixed per tablet in a polybag, and the mixed powder was tableted at a tableting pressure of 13.2 kN using a rotary tableting press (KIKUSUI SEISAKUSHO LTD., VELA5).

[Evaluation of Effect of Suppressing Bitterness]

The effect of suppressing bitterness was evaluated by three testers by containing 300 mg of granules of Example 1 or Comparative Example 1 in the mouth of the testers, and the effect of the bitterness masking was evaluated. Although the granule of Example 1 had a lower content of the hydrophobic polymer as compared with the granule of Comparative Example 1, the bitterness of the granule of Example 1 could be suppressed.

Although about 150 minutes was required to form the undercoat layer 95 in Comparative Example 1, the time required to form the gelling substance-containing layer 15 was only about 15 minutes in Example 1. Therefore, it was clarified that the production time of the granule of Example 1 can be greatly reduced.

Example 2

256 g of hydrous silicon dioxide (Fuji Silysia Chemical Ltd., Sylopure® P100) was used as the core substance 11, and 384 g of stearic acid (NOF CORPORATION, Sakura Fine Powder) was used as the first melt component. Hydrous silicon dioxide and stearic acid were poured into a high-speed stirring granulator (Fukae Industrial Co., Ltd., high-speed mixer, FS-GS-5 J), and granulated for 11 minutes at an agitator rotation speed of 300 rpm, a chopper rotation speed of 1500 rpm, and a water temperature of about 80° C. At this time, the temperature of the additive was about 70° C.

80.0 g of the core substance disposed with the melt component layer 12 on the surface, 248.12 g of sitagliptin phosphate as the active ingredient, and 24.0 g of aminoalkyl methacrylate copolymer E (Evonik Roehm, EUDRAGIT® EPO) as the second melt component were poured into a rotor fluidized bed granulator (Powrex Corporation, Model: MP-01), and granulation was performed at an air supply temperature of 80.0 to 85.0° C. and a rotor rotation speed of 400 rpm. At this time, the temperature of the additive was about 60° C.

352.12 g of the core substance disposed with the active ingredient-containing layer 13 on the surface, 32.0 g of carboxy vinyl polymer (Lubrizol Advanced Materials, Inc., CARBOPOL® 971P NF), and 6.0 g of sucralose (San-Ei Gen F.F.I., Inc., P) were poured into a rotor fluidized bed granulator (Powrex Corporation, Model: MP-01), and dry coating was performed at an air supply temperature of 80.0 to 85.0° C. and a rotor rotation speed of 400 rpm. At this time, the temperature of the additive was about 60° C. The carboxyvinyl polymer has a viscosity of 4000 to 11000 mPa/s in a 0.5% aqueous solution.

48.0 g of dried methacrylic acid copolymer LD (Evonik Roehm, EUDRAGIT® L100-55), 1.44 g of hypromellose (Shin-Etsu Chemical Co., Ltd., TC-5® E), 14.4 g of talc (FUJI TALC INDUSTRIAL CO., LTD., ML115), and 4.8 g of light anhydrous silicic acid (Freund Corporation, Adsolider® 101) were dispersed in 560 g of ethanol and 96.0 g of purified water to prepare a coating liquid. 390.12 g of the core substance disposed with the gelling substance-containing layer 15 on the surface was poured into a rotor fluidized bed granulator (Powrex Corporation Model: MP-01) and sprayed with a coating agent to form the hydrophobic polymer-containing layer 17.

32.0 g of D-mannitol (Mitsubishi Shoji Foodtech Co., Ltd., Mannitol P) and 4.0 g of sucralose (San-Ei Gen F.F.I., Inc., P) were dissolved in 280 g of purified water to prepare a coating liquid. 458.76 g of the core substance disposing the hydrophobic polymer-containing layer 17 on the surface was poured into a rotor fluidized bed granulator (Powrex Corporation, Model: MP-01) and sprayed with a coating agent to form the overcoat layer 19 to obtain the particle of Example 2.

140 mg of D-Mannitol-crystalline cellulose-low substitution hydroxypropyl cellulose-crospovidone granules constituting of 113.4 mg of D-Mannitol (Mitsubishi Shoji Foodtech, Co., Ltd, Mannitol P), 14.0 mg of crystalline cellulose (Asahi Kasei Corp., CEOLUS® PH-101), 7.0 mg of low substitution hydroxypropyl cellulose (Shin-Etsu Chemical Co., Ltd., L-HPC® NDB-022), 2.8 mg of crospovidone (BASF, Kollidon® CL-F), and 2.8 mg of crospovidone (BASF, Kollidon® CL-M), 247.38 mg of particles of Example 2, 34.62 mg of D-Mannitol (Freund Corporation, Granutol), 20.0 mg of silica-treated crystalline cellulose (JRS PHARMA, PROSOLV® SMCC50), 10.0 mg of crospovidone (BASF, Kollidon® CL-F), 16.0 mg of magnesium aluminometasilicate (Fuji Chemical Industries Co., Ltd., Neusilin® UFL-2.), and 12.0 mg of sodium stearyl fumarate (Rettenmaier Japan, Co., Ltd., PRUV®) were mixed per tablet in a polybag, and the mixed powder was tableted at a tableting pressure of 11.3 kN using a rotary tableting press (KIKUSUI SEISAKUSHO LTD., VELA5).

Example 3

The gelling substance-containing layer 15 of Example 3 was formed by the same method as in Example 2, except that 352.12 g of the core substance disposed with the active ingredient-containing layer 13 of Example 2 on the surface was used, and carboxy vinyl polymer was changed to 24.0 g and sucralose was changed to 6.2 g.

The hydrophobic polymer-containing layer 17 of Example 3 was formed by the same method as in Example 2 by using 382.52 g of the core substance disposed with the gelling substance-containing layer 15 on the surface.

The overcoat layer 19 of Example 3 was formed by the same method as in Example 2, except that 451.2 g of the core substance disposed with the hydrophobic polymer-containing layer 17 on the surface was used, and sucralose (San-Ei Gen F.F.I., Inc., P) was changed to 4.8 g to obtain the particle of Example 3.

160 mg of D-Mannitol-crystalline cellulose-low substitution hydroxypropyl cellulose-crospovidone granules, 243.98 mg of particles of Example 3, 29.22 mg of D-Mannitol (Granutol® F), 16.0 mg of silica-treated crystalline cellulose (JRS PHARMA, PROSOLV® SMCC50), 10.0 mg of crospovidone (BASF, Kollidon® CL-F), 16.0 mg of magnesium aluminometasilicate (Fuji Chemical Industries Co., Ltd., Neusilin® UFL-2), and 4.8 mg of sodium stearyl fumarate (Rettenmaier Japan, Co., Ltd., PRUV®) were mixed per tablet in a polybag, and the mixed powder was tableted at a tableting pressure of 11.3 kN using a rotary tableting press (KIKUSUI SEISAKUSHO LTD., VELA5).

Example 4

The gelling substance-containing layer 15 of Example 4 was formed by the same method as in Example 2, except that 352.12 g of the core substance disposed with the active ingredient-containing layer 13 of Example 2 on the surface was used, and carboxy vinyl polymer was changed to 24.0 g, and sucralose was changed to 4.0 g of hydrous silicon dioxide (Evonik, CARPLEX® #80).

62.0 g of dried methacrylic acid copolymer LD (Evonik Roehm, EUDRAGIT® L100-55), 2.4 g of hypromellose (Shin-Etsu Chemical Co., Ltd., TC-5® E), and 8.0 g of hydrous silicon dioxide (Evonik, CARPLEX® #80) were dispersed in 640 g of ethanol and 160 g of purified water to prepare a coating liquid. 380.12 g of the core substance disposed with the gelling substance-containing layer 15 on the surface was poured into a rotor fluidized bed granulator (Powrex Corporation, Model: MP-01) and sprayed with a coating agent to form the hydrophobic polymer-containing layer 17 of Example 4.

The overcoat layer 19 of Example 3 was formed by the same method as in Example 2, except that 454.6 g of the core substance disposed with the hydrophobic polymer-containing layer 17 on the surface was used and sucralose (San-Ei Gen F.F.I., Inc., P) was changed to 8.0 g to obtain the particle of Example 4.

176 mg of D-mannitol-crystalline cellulose-low-substitution hydroxypropyl cellulose-crospovidone granules, 247.26 mg of particle of Example 4, 10.74 mg of D-mannitol (Freund Corporation, Granutol® F), 10.0 mg of crospovidone (BASF, Kollidon® CL-F), 24.0 mg of magnesium aluminometasilicate (Fuji Chemical Industries Co., Ltd., Neusilin® UFL-2), and 12.0 mg of sodium stearyl fumarate (Rettenmaier Japan, Co., Ltd., PRUV®) were mixed per tablet in a polybag, and the mixed powder was tableted at a tableting pressure of 11.3 kN using a rotary tableting press (KIKUSUI SEISAKUSHO LTD., VELA5).

Example 5

The gelling substance-containing layer 15 of Example 5 was formed by the same method as in Example 2, except that 352.12 g of the core substance disposed with the active ingredient-containing layer 13 of Example 2 on the surface was used, and the carboxy vinyl polymer was changed to 24.0 g and no sucralose was added.

80.0 g of dried methacrylic acid copolymer LD (Evonik Roehm, EUDRAGIT® RSPO) were dispersed in 400 g of ethanol and 100.0 g of purified water to prepare a coating liquid. 376.12 g of core substance disposed with the gelling substance-containing layer 15 on the surface was poured into a rotor fluidized bed granulator (Powrex Corporation, Model: MP-01) and sprayed with a coating agent to form the hydrophobic polymer-containing layer 17 of Example 5.

The overcoat layer 19 of Example 5 was formed by the same method as in Example 4 by using 456.2 g of the core substance disposed with the hydrophobic polymer-containing layer 17 on the surface to obtain the particle of Example 5.

160 mg of D-mannitol-crystalline cellulose-low substitution hydroxypropyl cellulose-crospovidone granules, 248.06 mg of particle of Example 5, 17.14 mg of D-Mannitol (Granutol® F), 17.14 mg of silica-treated crystalline cellulose (JRS PHARMA, PROSOLV® SMCC50), 10.0 mg of crospovidone (BASF, Kollidon® CL-F), 24.0 mg of magnesium aluminometasilicate (Fuji Chemical Industries Co., Ltd., Neusilin® UFL-2), and 4.8 mg of magnesium stearate (Taihei Chemical Industrial Co., Ltd.) were mixed per tablet in a polybag, and the mixed powder was tableted at a tableting pressure of 11.3 kN using a rotary tableting press (KIKUSUI SEISAKUSHO LTD., VELA5).

Comparative Example 2

A core substance disposed with the melt component layer 12 on the surface was obtained by the same method as in Example 2, except that stearic acid (NOF CORPORATION, Sakura fine powder) was changed to stearic acid (NOF CORPORATION, vegetable).

A core substance disposed with the active ingredient-containing layer 13 of Comparative Example 2 on the surface was obtained by the same method as in Example 2, except that a core substance disposed with the melt component layer 12 of Comparative Example 2 on the surface was used.

32.0 g of hypromellose (Shin-Etsu Chemical Co., Ltd., TC-5® E) and 1.6 g of light anhydrous silicic acid (Freund Corporation, Adsolider® 101) were dispersed in 640 g of purified water to prepare a coating liquid. 352.12 g of the core substance disposed with the active ingredient-containing layer 13 of Comparative Example 2 on the surface was poured into a rotor fluidized bed granulator (Powrex Corporation, Model: MP-01) and sprayed with a coating agent to form the undercoat layer 95.

48.0 g of dried methacrylic acid copolymer LD (Evonik Roehm, EUDRAGIT® L100-55), 1.92 g of hypromellose (Shin-Etsu Chemical Co., Ltd., TC-5® E), 14.2 g of talc (FUJI TALC INDUSTRIAL CO., LTD., ML115), and 4.8 g of light anhydrous silicic acid (Freund Corporation, Adsolider® 101) were dispersed in 600 g of ethanol and 120.0 g of purified water to prepare a coating liquid. 385.72 g of the core substance disposed with the undercoat layer 95 on the surface was poured into a rotor fluidized bed granulator (Powrex Corporation, Model: MP-01) and sprayed with a coating agent to form the hydrophobic polymer-containing layer 17.

48.0 g of D-mannitol (Mitsubishi Shoji Foodtech Co., Ltd., Mannitol P) and 8.0 g of sucralose (San-Ei Gen F.F.I., Inc., P) were dissolved in 400 g of purified water to prepare a coating liquid. 454.84 g of the core substance disposed with the hydrophobic polymer-containing layer 17 on the surface was poured into a rotor fluidized bed granulator (Powrex Corporation, Model: MP-01) and sprayed with a coating agent to form the overcoat layer 19 to obtain the particle of Comparative Example 2.

152 mg of D-Mannitol-crystalline cellulose-low substitution-hydroxypropyl cellulose-crospovidone granules, 255.42 mg of particle of Comparative Example 2, 34.58 mg of D-Mannitol (Freund Corporation, Granutol® F), 16.0 mg of silica-treated crystalline cellulose (JRS PHARMA, PROSOLV® SMCC50), 10.0 mg of crospovidone (BASF, Kollidon® CL-F), 16.0 mg of magnesium aluminometasilicate (Fuji Chemical Industries Co., Ltd., Neusilin® UFL-2), and sodium stearyl fumarate (Rettenmaier Japan, Co., Ltd., PRUV) were mixed per tablet in a polybag, and the mixed powder was tableted at a tableting pressure of 11.3 kN using a rotary tableting press (KIKUSUI SEISAKUSHO LTD., VELA5).

Comparative Example 3

80.0 g of dried methacrylic acid copolymer LD (Evonik Roehm, EUDRAGIT® L100-55), 3.2 g of hypromellose (Shin-Etsu Chemical Co., Ltd., TC-5® E), 24.0 g of talc (FUJI TALC INDUSTRIAL CO., LTD., ML115), and 8.0 g of light anhydrous silicic acid (Freund Corporation, Adsolider® 101) were dispersed in 1000 g of ethanol and 200.0 g of purified water to prepare a coating liquid. 385.72 g of the core substance disposed with the undercoat layer 95 of Comparative example 2 on the surface was poured into a rotor fluidized bed granulator (Powrex Corporation, Model: MP-01) and sprayed with a coating agent to form the hydrophobic polymer-containing layer 17.

The overcoat layer 19 was formed by the same method as in Comparative Example 2 by using 500.92 g of the core substance disposed with the hydrophobic polymer-containing layer 17 of Comparative Example 3 on the surface to obtain the particle of Comparative Example 3.

The preparation of Comparative Example 3 was obtained by the same method as in Comparative Example 2, except that D-mannitol-crystalline cellulose-low substitution hydroxypropyl cellulose-crospovidone granules was changed to 128 mg, the particle of Comparative Example 3 was changed to 278.46 mg, and D-mannitol (Freund Corporation, Granutol® F) was changed to 35.54 mg per tablet.

[Evaluation of Effect of Suppressing Bitterness]

Figure 3:
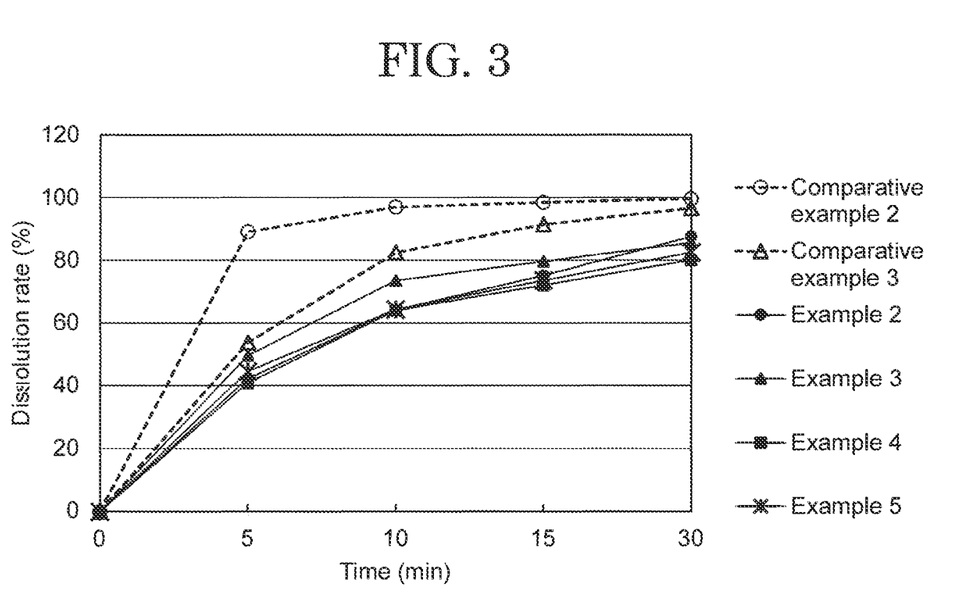
FIG. 3 is a diagram showing a dissolution rate of sitagliptin phosphate in a preparation of an example of the present invention.

The elution property of sitagliptin phosphate were evaluated for the preparations of Examples 2 to 5 and Comparative Examples 2 to 3 in accordance with the dissolution test method (paddle method) of the Japanese Pharmacopoeia Seventeenth Edition. 900 ml of water was used as a test solution. The rotation speed of the paddle was 50 rpm. The dissolution rate of sitagliptin phosphate was measured at 5, 10, 15 and 30 minutes after the start of the test. The measurement results of the dissolution rate of sitagliptin phosphate are shown in FIG. 3. The preparations of Examples 2 to 5 using carbopol which is a gelling substance in the gelling substance-containing layer 15 suppressed elution of sitagliptin phosphate as compared with the preparations of Comparative Examples 2 to 3 having the undercoat layer 95 containing hypromellose, and it was clarified that the carbopol functions in suppressing elution of sitagliptin phosphate (bitterness suppress).

In particular, although the preparations of Examples 2 to 4 have smaller contents of a hydrophobic polymer (Eudragit® L100-55) in the hydrophobic polymer-containing layer 17 than the preparation of Comparative Example 3, the elution of the sitagliptin phosphate is suppressed, and bitterness of sitagliptin phosphate can be suppressed with a small coating amount (reduction in the time for forming the gelling substance-containing layer 15) by containing the gelling substance in the gelling substance-containing layer 15. Comparing the preparation of Example 2 and the preparation of Example 5, the same elution behavior of sitagliptin phosphate was exhibited despite the fact that the content of the hydrophobic polymer in the hydrophobic polymer-containing layer 17 was reduced to 60% by weight in the preparation of Example 2. From this result, it was clarified that the suppression of bitterness can be achieved in the preparation according to the present invention when the gelling substance: the hydrophobic polymer=2:3 to 3:8. From the viewpoint of reducing the production time, it is preferable that the content of hydrophobic polymer in the hydrophobic polymer-containing layer 17 is as small as possible.

Example 6

256 g of hydrous silicon dioxide (Fuji Silysia Chemical Ltd., Sylopure® P100) was used as the core substance 11, and 384 g of stearic acid (NOF CORPORATION, Sakura Fine Powder) was used as the first melt component. Hydrous silicon dioxide and stearic acid were poured into a high-speed stirring granulator (Fukae Industrial Co., Ltd., high-speed mixer, FS-GS-5 J), and granulated for 11 minutes at an agitator rotation speed of 300 rpm, a chopper rotation speed of 1500 rpm, and a water temperature of about 80° C. At this time, the temperature of the additive was about 70° C.

A core substance disposed with the active ingredient-containing layer 13 on the surface was obtained by the same method as in Example 2 by using 80.0 g of the core substance disposed with the melt component layer 12 on the surface.

319.70 g of the core substance disposed with the active ingredient-containing layer 13 on the surface and 20.4 g of polyethylene oxide (Dow Chemical, POLYOX® WSR N-60K) were poured into a rotor fluidized bed granulator (Powrex Corporation, Model: MP-01), and dry coating was performed at an air supply temperature of 80.0 to 85.0° C. and a rotor rotation speed of 400 rpm. At this time, the temperature of the additive was about 60° C. Polyethylene oxide has a viscosity of 2000 to 4000 mPa/s in a 2% aqueous solution.

The hydrophobic polymer-containing layer 17 of Example 6 was formed by the same method as in Example 4, except that 390.12 g of the core substance disposed with the gelling substance-containing layer 15 of Example 6 on the surface was used.

The particle of Example 6 was obtained by the same method as in Example 4, except that 458.76 g of the core substance disposed with the hydrophobic polymer-containing layer 17 of Example 6 on the surface was used.

Comparative Example 4

256 g of hydrous silicon dioxide (Fuji Silysia Chemical Ltd., Sylopure® P100) was used as the core substance 11, 153.6 g of stearic acid (NOF CORPORATION, vegetable) and 204.8 g of stearic acid (BASF Pharma, Kolliwax® S Fine) were used as the first melt component. Hydrous silicon dioxide and stearic acid were poured into a high-speed stirring granulator (Fukae Industrial Co., Ltd., high-speed mixer, FS-GS-5 J), and granulated for 11 minutes at an agitator rotation speed of 300 rpm, a chopper rotation speed of 1500 rpm, and a water temperature of about 80° C. At this time, the temperature of the additive was about 70° C.

80.0 g of core substance disposed with the melt component layer 12 on the surface, 210.9 g of sitagliptin phosphate as the active ingredient, and 27.2 g of aminoalkyl methacrylate copolymer E (Evonik Roehm, EUDRAGIT® EPO) as the second melt component were poured into a rotor fluidized bed granulator (Powrex Corporation, Model: MP-01), and granulation was performed at an air supply temperature of 80.0 to 85.0° C. and a rotor rotation speed of 400 rpm. At this time, the temperature of the additive was about 60° C.

24.0 g of hypromellose (Shin-Etsu Chemical Co., Ltd., TC-5® E) and 1.2 g of hydrous silicon dioxide (Evonik, CARPLEX® #80) were dispersed in 360 g of purified water to prepare a coating liquid. 376.12 g of the core substance disposed with the active ingredient-containing layer 13 of Comparative Example 2 on the surface was poured into a rotor fluidized bed granulator (Powrex Corporation, Model: MP-01) and sprayed with a coating agent to form the undercoat layer 95.

76.0 g of dried methacrylic acid copolymer LD (Evonik Roehm, EUDRAGIT® L100-55), 2.4 g of hypromellose (Shin-Etsu Chemical Co., Ltd., TC-5® E), and 14.2 g of titanium oxide (Toho Titanium, Co., Ltd., NA61) were dispersed in 600 g of ethanol and 120.0 g of purified water to prepare a coating liquid. 401.32 g of the core substance disposed with the undercoat layer 95 on the surface was poured into a rotor fluidized bed granulator (Powrex Corporation, Model: MP-01) and sprayed with a coating agent to form the hydrophobic polymer-containing layer 17.

32.0 g of D-mannitol (Mitsubishi Shoji Foodtech Co., Ltd., Mannitol P) and 12.0 g of sucralose (San-Ei Gen F.F.I., Inc., P) were dissolved in 280 g of purified water to prepare a coating liquid. 494.12 g of the core substance disposed with the hydrophobic polymer-containing layer 17 on the surface was poured into a rotor fluidized bed granulator (Powrex Corporation, Model: MP-01) and sprayed with a coating agent to form the overcoat layer 19 to obtain the particle of Comparative Example 4.

[Evaluation of Effect of Suppressing Bitterness]

The effect of suppressing bitterness was evaluated for the particles of Examples 4 and 6 and Comparative Example 4. Specifically, the effect of suppressing bitterness was evaluated by two testers by containing 300 mg of granules of Examples 4 and 6 or Comparative Example 4 in the mouths of the testers, and the effect of suppressing bitterness was evaluated. The results of evaluation of the effect of suppressing bitterness of the particles of Examples 4 and 6 and Comparative Example 4, and the formation times of the gelling substance-containing layer 15 and the undercoat layer 95 are shown in Table 1.

TABLE 1

|  | Example 4 | Example 6 | Comparative Example 4 |
| --- | --- | --- | --- |
| Additive | Carboxyvinyl polymer | Polyethylene oxide * | hypromellose |
| Bitterness | ○ | ○ | x |
| Layer formation time | 15 minutes | 15 minutes | 120 minutes |

Since the particles of Examples 4 and 6 contained a gelling substance in the gelling substance-containing layer 15, when contained in the mouth of the testers, the gelling substance swelled by saliva permeating from the gap of the hydrophobic polymer-containing layer 17, thereby suppressing bitterness derived from the active ingredient. Since the particle of Comparative Example 4 did not contain a gelling substance in the undercoat layer 95, bitterness could not be suppressed. When comparing the amount of the hydrophobic polymer (Eudragit® L100-55) added in the hydrophobic polymer-containing layer 17 of the particles of Examples 4 and 6 and Comparative Example 4, the amounts were 32 mg and 38 mg, respectively, and it was found that the gelling substance contributed to suppressing bitterness, since Examples 4 and 6 suppressed the bitterness even though the amount of the hydrophobic polymer contained in the particles of Examples 4 and 6 was smaller than that of the particles of Comparative Example 4. From the evaluation result of the effect of suppressing bitterness, not only the production time of the gelling substance-containing layer 15 is reduced, but also the amount of the hydrophobic polymer contained in the hydrophobic polymer-containing layer 17 can be reduced as compared with the conventional technology in the particle according to the present invention. Although the difference between the effect of suppressing bitterness of the particles of Example 4 and the effect of suppressing bitterness of the particles of Example 6 was not observed, in principle, it was shown that any additive which is generally treated as a gelling substance and can be dry coated can be applied to the particle according to the present invention.

An embodiment of the present invention may provide a granule capable of sufficiently masking bitterness. Alternatively, an embodiment of the present invention may provide a preparation containing the granule capable of sufficiently masking bitterness. Alternatively, an embodiment of the present invention may provide a production method of the granule capable of sufficiently masking bitterness. Alternatively, an embodiment of the present invention may provide a production method of a preparation containing the granule capable of sufficiently masking bitterness.

What is claimed is:

1. A granule comprising:
    a core substance;
    a melt component layer consisting of a first melt component, the melt component layer disposed on a surface of the core substance;
    an active ingredient-containing layer containing a second melt component and an active ingredient, the active ingredient-containing layer disposed on a surface of the melt component layer;
    a gelling substance-containing layer disposed on a surface where the second melt component and the active ingredient are disposed; and
    a hydrophobic polymer-containing layer disposed on a surface of the gelling substance-containing layer,
    wherein the core substance is composed of an adsorbent material selected from a group consisting of amberlite IRP-64, ion exchange resin, kaolin, calcium carmellose, hydrous silicon dioxide, magnesium silicate, light anhydrous silicic acid, light liquid paraffin, diatomaceous earth, synthetic aluminum silicate, aluminum oxide, aluminum hydroxide, absorbent cotton, magnesium carbonate, precipitated calcium carbonate, dextrin, silicon dioxide, composite aluminum silicate potassium grain, bentonite, polyethylene fiber, magnesium aluminate metasilicate, and medicinal charcoal,
    the first melt component contained in the melt component layer is selected from a group consisting of glycerin monostearate, lauromacrogol, and stearic acid,
    the second melt component in the active ingredient-containing layer is selected from a group consisting of stearic acid, glyceryl monostearate, carnauba wax, hydrogenated oil, lauromacrogol, palmitic acid, cetyl alcohol, aminoalkyl methacrylate copolymer E, ammonioalkyl methacrylate copolymer, dried methacrylic acid copolymer, hypromellose acetate succinate ester, polyvinylpyrrolidone, and polyvinyl acetal diethyl aminoacetate and, wherein the gelling substance-containing layer includes a gelling substance having a viscosity of 10 mPa/s or more in a 2% aqueous solution.

2. The granule according to claim 1, further comprising:
    an overcoat layer disposed on a surface of the hydrophobic polymer-containing layer.

3. The granule according to claim 1, wherein
    the gelling substance-containing layer includes one or more gelling substances selected from a group consisting of sodium carboxymethyl cellulose, polyethylene oxide, sodium polyacrylate, sodium alginate, propylene glycol alginate, xanthan gum, carrageenan, guar gum, tara gum, pectin, hydroxypropyl cellulose, hydroxyethyl cellulose, methyl cellulose, carboxyvinyl polymer, locust bean gum, tamarind seed gum, gum arabic, karaya gum, agar, gelatin, polyvinyl alcohol, and a copolymer with polyvinyl alcohol as a part.

4. The granule according to claim 1, wherein
    the hydrophobic polymer-containing layer includes one or more hydrophobic polymers selected from ethyl cellulose, acetyl cellulose, cellulose acetate phthalate, carboxymethyl ethyl cellulose, hydroxypropyl methyl cellulose acetate succinate, hydroxypropyl methylcellulose phthalate, dimethylaminoethyl methacrylate/methyl methacylate copolymer, methyl acrylate/methacrylic acid copolymer, ethyl acrylate/methyl methacrylate copolymer dispersion, aminoalkyl methacrylate copolymer RS, dried methacrylic acid copolymer LD, aminoalkyl methacrylate copolymer E, methacrylic acid copolymer L, methacrylic acid copolymer S, and polyvinyl acetal diethylaminoacetate.

5. The granule according to claim 4, wherein the content ratio of the gelling substance contained in the gelling substance-containing layer to the hydrophobic polymer contained in the hydrophobic polymer-containing layer is in a range of 2:3 to 3:8.

6. A preparation comprising:

the granule according to claim 1; and one or more pharmaceutically acceptable additives.

* * * * *